United States Patent [19]

Ichimura

[11] 4,350,833
[45] Sep. 21, 1982

[54] TEREPHTHALDIALDEHYDE MONOACETAL AND METHOD FOR MANUFACTURE THEREOF

[76] Inventor: Kunihiro Ichimura, 306-302, Matsushiro 3 chome, Yatabemachi, Tsukuba-gun, Ibaragi-ken, Japan

[21] Appl. No.: 229,076

[22] Filed: Jan. 28, 1981

[30] Foreign Application Priority Data

Mar. 29, 1980 [JP] Japan .................................. 55/40958

[51] Int. Cl.³ .................... C07C 47/548; C07C 45/61
[52] U.S. Cl. ................................. 568/433; 568/442; 568/336; 568/337; 562/470; 260/465 D; 546/347; 546/152
[58] Field of Search .............................. 568/433, 442

[56] References Cited

PUBLICATIONS

Verkataramn et al., Jour. Org. Chem., vol. 44 (1979), 3082.

Primary Examiner—Bernard Helfin

[57] ABSTRACT

Terephthaldialdehyde monoacetals represented by the general formula:

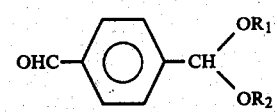

(wherein, $R_1$ and $R_2$ are lower alkyl groups) are novel compounds, and they are produced by the reaction of terephthaldialdehyde with alcohols in the presence of a strongly acidic substance as a catalyst.

7 Claims, No Drawings

TEREPHTHALDIALDEHYDE MONOACETAL AND METHOD FOR MANUFACTURE THEREOF

BACKGROUND OF THE INVENTION

This invention relates to novel terephthaldialdehyde monoacetals useful as the raw material for water-soluble photosensitive resins, and to a method for the manufacture of these novel compounds.

It is well known that the reaction of terephthaldialdehyde with dihydric alcohols in the presence of an acid catalyst produces terephthaldialdehyde diacetals.

S. D. Verkataramn, Z. H. Cleveland and D. E. Pearson, J. Org. Chem, 44, 3082(1979) for example, report that the compounds

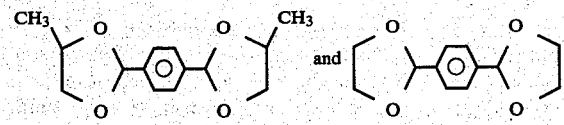

were obtained by using the dialdehyde and the corresponding glycols in the presence of p-toluenesulfonic acid.

The reactions heretofore known as being capable of producing terephthaldialdehyde monoacetals are limited to those reported by J. Y. Wong, C. Manning and C. C. Leznoff in Angew Chem., 86, 743 (1974), by C. C. Leznoff and J. Y. Wong in Can. J. Chem., 51, 3756 (1937) and by G. P. Sokolou and S. Hillers in Khim. Geterosiki Soedin., 1330 (1976). All these reactions are directed to production of cyclic acetals. The first two studies cover the production of cyclic acetals through the reaction of the formula:

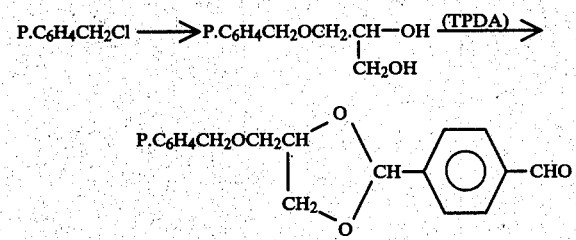

(P: polystyrene, TPDA: terephthaldialdehyde) The last study covers the production due to the reaction of the formula:

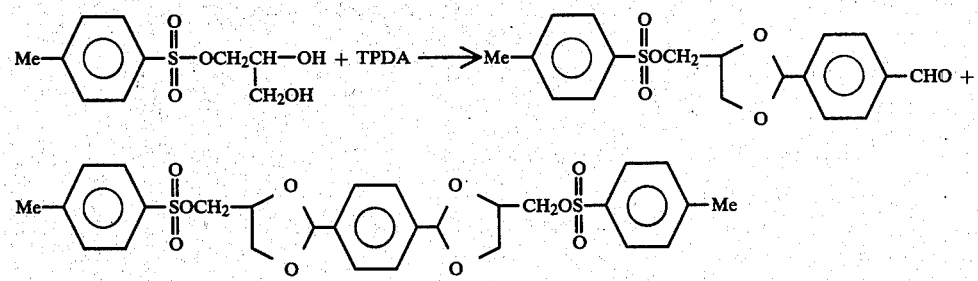

Water-soluble, highly photosensitive resins which have polyvinyl alcohols as their backbone high polymers find utility in a wide vareiety of applications. To produce such water-soluble, highly photosensitive resins having polyvinyl alcohols as their backbone high polymers, it becomes necessary to cause highly photosensitive olefin compounds such as cinnamoyl compounds, chalcone compounds and styrylpyridium compounds which possess an acetalized formyl group to react with polyvinyl alcohols. For the production of olefin compounds possessing an acetalized formyl group, it has now become necessary to provide terephthaldialdehyde monoacetals which are non-cyclic in structure, namely which contain only chain groups. This invention aims to satisfy this need.

One object of this invention is to provide terephthaldialdehyde monoacetals which are non-cyclic in structure, namely which contain only chain groups, as novel compounds.

Another object of this invention is to provide a method for the manufacture of the novel compounds mentioned above.

SUMMARY OF THE INVENTION

To accomplish the objects described above according to the present invention, there are provided terephthaldialdehyde monoacetals represented by the general formula:

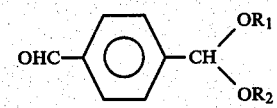

(wherein, $R_1$ and $R_2$ are lower alkyl groups) and a method for the manufacture of the compounds mentioned above, which method comprises causing terephthaldialdehyde to react with a monohydric alcohol in the presence of a strongly acidic substance as a catalyst.

DETAILED DESCRIPTION OF THE INVENTION

The terephthaldialdehyde monoacetals of the present invention are represented by the general formula:

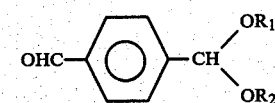

(wherein, $R_1$ and $R_2$ each denote a lower alkyl of not more than 5 carbon atoms, methyl, ethyl and propyl groups being examples).

The monohydric alcohols which are usable for the method of the present invention are lower aliphatic alcohols of three or less carbon atoms such as, for example, methyl alcohol, ethyl alcohol and propyl alcohol.

When dihydric alcohols are used for the method of the present invention, the yield of monoacetal decreases and that of diacetal increases. This will be clarified in Comparative Example described later.

Examples of the strongly acidic substances which are usable for this method include strong inorganic acids such as phosphoric acid, sulfuric acid and hydrohalogenic acids, strong organic acids such as benzenesulfonic acid and p-toluenesulfonic acid, and strongly acidic ion-exchange resins substituted to strongly acid residues such as sulfonic acid and phosphoric acid.

The ratio between the amount of terephthaldialdehyde and that of the monohydric alcohol to be used in the reaction of this invention is desired to fall within the range of from 1 to 20 mols, preferably from 2 to 12 mols, of the monohydric alcohol to 1 mol of the terephthaldialdehyde.

When the amount of the monohydric alcohol does not reach 1 mol per mol of the terephthaldialdehyde, the amount of the unaltered terephthaldialdehyde is so large as to lower the yield of the monoacetal intolerably. When the amount exceeds 20 mols, the acetalization proceeds excessively and the amount of the diacetal increases and the yield of the monoacetal decreases intolerably.

The strongly acidic substance is added in an amount falling within the range of from 0.01 g to 10 g (or $10^{-5}$ mol to $10^{-2}$ mol) to 1 mol of the terephthaldialdehyde. In the case of the ion-exchange resin, the amount thereof to be added in the batch system is adjusted so that the strongly acidic residue occurs in equivalent of from $10^{-5}$ to $10^{-2}$ based on 1 mol of the terephthaldialdehyde. When the strongly acidic residue occurs in an amount less than the lower limit indicated above, the reaction effect is less than is expected. When it occurs in an amount greater than the upper limit, removal of such acidic residue proves to be a difficult job. In the continuous system, however, the amount of the ion-exchange resin to be added may be adjusted so that the strongly acidic residue occurs in equivalent of $10^{-3}$ or more, although the reaction effect is affected by the velocity of the reactant which passes through the ion-exchange resin.

The reaction can be effected by simply dissolving the terephthaldialdehyde in the monohydric alcohol without use of any solvent. Optionally, the reaction mixture may be diluted with an inactive organic solvent such as, for example, methylene chloride, benzene or tetrahydrofuran.

According to the method of this invention, the conversion to the monoacetal proceeds very quickly at room temperature or an elevated temperature up to 100° C.

In a batchwise operation, the method of this invention can be carried out by adding the strongly acidic substance to the mixed solution of the terephthaldialdehyde and the monohydric alcohol and stirring the resultant mixture for a fixed length of time and thereafter separating the reaction product from the reaction mixture. When a strongly acidic ion-exchange resin is used as the strongly acidic substance, the reaction can be carried out either in a continuous operation or in a batchwise operation. In the former case, the reaction can be effected by feeding the mixed solution of the terephthaldialdehyde and the monohydric alcohol into a column packed with the strongly acidic ion-exchange resin. The effluent from the column contains a terephthaldialdehyde monoacetal formed in a high yield.

Since this continuous operation permits the terephthaldialdehyde monoacetal to be produced at a constant yield over a very long period, it is suitable for commercial production of the novel compound.

In the reaction solution obtained after completion of the reaction, the terephthaldialdehyde monoacetal is present in conjunction with the unaltered portions of the raw material, terephthaldialdehyde and monohydric alcohol, and terephthaldialdehyde diacetal. Since these compounds all have different boiling points, they can be separated by distillation. Thus, terephthaldialdehyde monoacetal of high purity can be obtained with ease.

The terephthaldialdehyde monoacetals of the present invention which are devoid of cyclic groups and are possessed only of chain groups, on being subjected to condensation with compounds possessing active methylene or active methyl group such as, for example, malonic acid, cyanoacetic acid, esters thereof, acetophenone, methoxyacetophenone, 1,4-dimethyl-pyridinium salt, 1,4-dimethyl-quinolium salt and 1,2-dimethyl-pyridinium salt, produce photosensitive compounds possessing an acetalized formyl group as enumerated below by way of illustration.

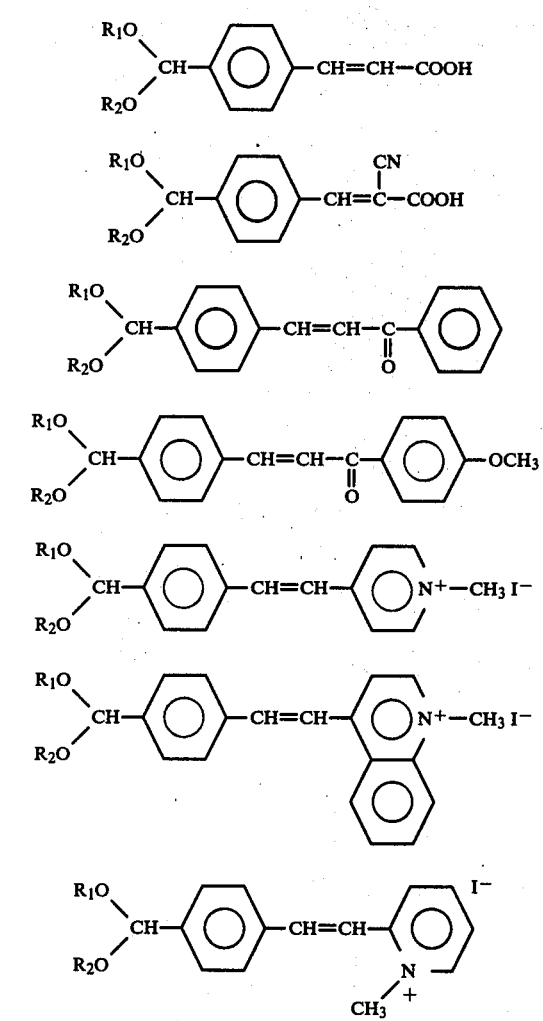

(wherein, $R_1$ and $R_2$ have the same meanings as defined above).

When such a photosensitive compound is caused to react with a polyvinyl alcohol or a partially saponified polyvinyl acetate in the presence of an acid catalyst, the acetalized formyl group undergoes acetal exchange reaction to form an acetal with the hydroxyl group of the polymer. Consequently, this reaction provides effective incorporation of a photosensitive group into the polymer and gives rise to a highly photosensitive water-soluble resin.

As described above, the terephthaldialdehyde monoacetals of the present invention are useful compounds as the raw material for water-soluble photosensitive resins. The method of the present invention permits such terephthaldialdehyde monoacetals to be produced in high yields by a simple procedure, and is suitable for commercial production of these compounds.

Now, the present invention will be described more specifically below with reference to working examples of the invention.

EXAMPLE 1

By heating, 100 g of terephthaldialdehyde and 330 g of ethanol were converted into a homogeneous solution. This solution and 2 g of a strongly acidic ion-exchange resin (sulfonated polystyrene beads of 100-200 mesh, marketed under the trademark "Dowex 50Wx8") added thereto were stirred at a temperature of about 25° C for two hours. The mixture was filtered to remove the resin beads, the filtrate was concentrated under a vacuum, and the residue was distilled under a vacuum. During the distillation, terephthaldialdehyde was first separated, then 70 g of terephthaldialdehyde monoethylacetal having a boiling point of 109°-111° C. (at 1 mmHg) was separated, and finally a small amount of terephthaldialdehyde diethylacetal having a boiling point of 127°-131° C. (at 1 mmHg) was distilled fractionally.

The yield of terephthaldialdehyde monoethylacetal based on the terephthaldialdehyde initially charged was 45.1%.

EXAMPLE 2

In a mixed solution of 20 ml of ethanol and 20 ml of dichloromethane, 2 g of terephthaldialdehyde was dissolved.

Separately, a column having an inside diameter of 10 mm was charged to a height of 3 cm with the same strongly acidic ion-exchange resin (exchange capacity about 5 meq/g) as used in Example 1 (packed amount 4 g). The solution prepared as mentioned above was fed to flow downward at a flow rate of about 5 ml/min. into the column maintained at about 25° C. At intervals, the effluent from the column was sampled and assayed by gas chromatography.

The gas chromatography was carried out with a column, PEG-20M, having a length of 1 m, with the column temperatures maintained in the range of from 135° to 170° C.

The results of the assay were as shown in Table 1.

TABLE 1

| Effluent sample (ml) | Yield (%) | | |
|---|---|---|---|
| | Terephthaldialdehyde | Monoacetal | Diacetal |
| 0-5 | 19 | 71 | 10 |
| 5-10 | 10 | 75 | 14 |
| 10-15 | 12 | 74 | 13 |
| 15-20 | 7 | 75 | 16 |
| 20-30 | 6 | 75 | 18 |
| 30-35 | 6 | 75 | 17 |

It will be noted from Table 1 that the monoacetal was formed continuously in a high yield.

When the acetalization was further continued in the same column, the monoacetal could be produced in approximately the same yield for a long period of time.

EXAMPLE 3

By heating, 10.0 g of terephthaldialdehyde and 20.6 g of ethanol were converted into a homogeneous solution. This solution and 200 mg of the same strongly acidic ion-exchange resin as used in Example 1 were mixed and then left to stand overnight at room temperature. Then, this mixture was stirred at 0° C. for 15 minutes. Subsequently, the resin was removed and the reaction mixture was assayed by the same gas chromatography as involved in Example 2.

The procedure described above was repeated, except that the stirring for 15 minutes was done at room temperature in one test run and at 70° C. in the other test run, instead of at 0° C. The reaction mixtures obtained in these test runs were similarly assayed by the gas chromatography.

The results were as shown in Table 2.

It is seen from Table 2 that the yield of monoacetal increased with the decreasing temperature of agitation.

TABLE 2

| Temperature of agitation (°C.) | Yield (%) | | |
|---|---|---|---|
| | Terephthaldialdehyde | Monoacetal | Diacetal |
| 0° C. | 14 | 81 | 5 |
| room temp. | 29 | 66 | 5 |
| 70° C. | 40 | 58 | 2 |

EXAMPLE 4

In 20 ml of dichloromethane, 1.5 g of terephthaldialdehyde was dissolved. In this solution, one of the monohydric alcohols indicated in Table 3 and 50 mg of the same strongly acidic ion-exchange resin as used in Example 1 were stirred overnight at room temperature.

The reaction products thus obtained were assayed by the same gas chromatography as involved in Example 2.

The results were as shown in Table 3.

It is seen from Table 3 that monoacetals were efficiently formed by using monohydric alcohols.

TABLE 3

| Alcohol | Alcohol/terephthaldialdehyde (molar ratio)* | Yield (%) | | |
|---|---|---|---|---|
| | | Terephthaldialdehyde | Monoacetal | Diacetal |
| Ethanol | 2.0 | 46 | 53 | 1 |
| | 4.0 | 41 | 57 | 2 |
| | 6.0 | 22 | 73 | 5 |
| | 10.0 | 15 | 76 | 8 |
| Iso-propanol | 2.0 | 45 | 54 | 0.6 |
| | 4.0 | 27 | 72 | 1.3 |
| | 6.0 | 18 | 77 | 4.7 |
| | 10.0 | 9 | 81 | 10 |

*Molar ratio of the hydroxyl group of the alcohol per mol of terephthaldialdehyde.

COMPARATIVE EXAMPLE

The procedure described in Example 4 was repeated, except that dihydric alcohols were used instead of the monohydric alcohols. The results were as shown in Table 4. It is seen from Table 4 that the yield of monoacetal decreased and that of diacetal increased in comparison with the yields of monoacetal and diacetal obtained in Example 4.

TABLE 4

| Alcohol | Alcohol/terephthaldialdehyde (molar ratio) | Yield (%) | | |
|---|---|---|---|---|
| | | Terephthaldialdehyde | Monoacetal | Diacetal |
| 1,2-propyleneglycol | 3.0 | 47 | 35 | 18 |
| | 4.0 | 43 | 36 | 22 |
| | 8.2 | 20 | 38 | 42 |
| | 12.0 | 11 | 38 | 50 |
| 1,3-propyleneglycol | 3.0 | 43 | 24 | 33 |
| | 8.0 | 39 | 19 | 42 |
| | 12.0 | 23 | 24 | 53 |

EXAMPLE 5

The procedure of Example 4 was repeated, except that 30 mg of p-toluenesulfonic acid was used as the catalyst, this catalyst was dissolved in the reaction system and left to stand overnight, then the reaction solution was neutralized with an aqueous potassium carbonate solution and then washed with water. The reaction product was assayed similarly. The results were substantially the same as those of Table 3.

EXAMLE 6

The procedure of Example 5 was faithfully repeated, except that 30 mg of phosphoric acid was used in the place of p-toluenesulfonic acid. The results were substantially the same as those obtained in Example 5.

What is claimed is:

1. A terephthaldialdehyde monoacetal represented by the general formula:

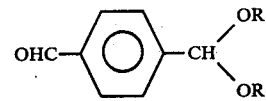

wherein R denotes a lower alkyl group.

2. The terephthaldialdehyde monoacetal according to claim 1, wherein R denotes a lower alkyl of not more than 5 carbon atoms.

3. A method for the manufacture of a terephthaldialdehyde monoacetal represented by the general formula:

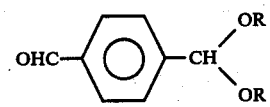

wherein R denotes a lower alkyl group, which comprises causing terephthaldialdehyde to react with a monohydric alcohol in the presence of a strongly acidic substance.

4. The method according to claim 3, wherein R denotes a lower alkyl of not more than 5 carbon atoms.

5. The method according to claim 3, wherein the strongly acidic substance is selected from the group consisting of strong inorganic acids, strong organic acids and strongly acidic ion-exchange resins possessing a strong acid residue.

6. The method according to claim 3, wherein the proportion between the amount of terephthaldialdehyde and that of the monohydric alcohol to be used in the reaction falls in the range of from 1 to 20 mols of the monohydric alcohol to 1 mol of the terephthaldialdehyde.

7. The method of claim 3, wherein the strongly acidic substance is added in an amount falling within the range of 0.01 g–10 g to one mol of the terephthaldialdehyde.

* * * * *

UNITED STATES PATENT AND TRADEMARK OFFICE
CERTIFICATE OF CORRECTION

PATENT NO. : 4,350,833
DATED : September 21, 1982
INVENTOR(S) : Kunihiro Ichimura It is certified that error appears in the above-identified patent and that said Letters Patent is hereby corrected as shown below:

On the title page,
Please insert the following Assignee:

[73] -- Agency of Industrial Science & Technology

Ministry of International Trade & Industry,

Tokyo, Japan--

Signed and Sealed this

Twenty-eighth Day of December 1982

[SEAL]

Attest:

GERALD J. MOSSINGHOFF

Attesting Officer      Commissioner of Patents and Trademarks